United States Patent
Weisz

[11] 3,975,514
[45] Aug. 17, 1976

[54] FLUORIDE MOUTH WASH COMPOSITIONS

[76] Inventor: Geraldine Fay Weisz, 2240 Harmain Road, Pittsburgh, Pa. 15235

[22] Filed: Jan. 13, 1975

[21] Appl. No.: 540,400

[52] U.S. Cl. .............................................. 424/52
[51] Int. Cl.² .......................................... A61K 7/18
[58] Field of Search ............................... 424/49–58

[56] References Cited
UNITED STATES PATENTS

| | | | |
|---|---|---|---|
| 2,913,373 | 11/1959 | Weisz et al. | 424/52 |
| 3,309,274 | 3/1967 | Brilliant | 424/58 |
| 3,886,266 | 5/1975 | Goldman et al. | 424/54 |

OTHER PUBLICATIONS

*Accepted Dental Therapeutics*, 35th Ed., published by American Dental Association, Chicago, 1973, p. 220.

*Primary Examiner*—Shep K. Rose
*Attorney, Agent, or Firm*—Buell, Blenko & Ziesenheim

[57] ABSTRACT

A mouth wash is provided having the capacity to prevent dental caries of teeth consisting essentially of an aqueous solution of a water soluble fluoride, sodium chloride and an anionic surface active wetting agent having no substantial effect on inactivation of the fluoride, the wetting agent and sodium chloride being present in minor amount relative to the fluoride and the fluoride being present in a concentration of about one gram per ounce of solution.

9 Claims, No Drawings

FLUORIDE MOUTH WASH COMPOSITIONS

This invention relates to means for preventing dental caries, and is more particularly concerned with a mouth wash preparation especially compounded for use in preventing the development of dental caries. It is an improvement on U.S. Pat. No. 2,913,373, issued Nov. 17, 1959.

It is known that the incidence of dental caries is considerably lower in those areas where the available supply of drinking water naturally contains fluoride in proper concentration, compared to those areas where such is not the case.

The use of sodium fluoride, either by ingestion from drinking water in which the same has been introduced or by topical application of solutions thereof, has a beneficial effect, if employed under adequately controlled conditions, in preventing or reducing the development of cavities in the teeth. To the extent that such use of sodium fluoride provides these benefits, they are ascribed to various theories, some of which, indeed, are controversial.

Numerous proposals have heretofore been made for securing the favorable prophylactic effect of fluorine on dental caries. These proposals, however, have proved either not practical, or efficacious, for one or more of a number of reasons.

Thus, it has been proposed in patent to Cross, U.S. Pat. No. 1,943,856, and in British patent to Lidgey, Pat. No. 3,034 of 1914 to incorporate sodium fluoride in dentifrices. Such dentifrices are not, however, efficacious, and suffer other objections, as pointed out in patent to Moss, U.S. Pat. No. 2,749,278. In the Moss patent it is proposed to avoid those objections by compounding tooth pastes from a fluorinated dialkalialkaline earth metal pyrophosphate containing specified amounts of chemically combined fluorine. Thus, the Moss proposal requires the antecedent step of preparing a suitable fluorinated pyrophosphate.

As in the topical application of fluoride by means of dentifrices, as referred to above, proposals heretofore made for the topical application of sodium fluoride in solution have not proved satisfactory, for reasons such as set forth, for example, in patent to Merckel U.S. Pat. No. 2,700,012. In that patent, it is sought to obtain both ingestion and surface application of soluble fluoride by means of a chewing gum made by mixing sodium fluoride into a gum base previously treated with a salt or other substance which reacts with the combined calcium salts or compounds naturally contained in the gum base, to yield a calcium compound at least as insoluble as calcium floride, thereby preventing the calcium or like compound from rendering the sodium fluoride incorporated in the treated gum base inactive for its intended prophylactic purpose.

It has also heretofore been suggested that water solutions of soluble fluoride be externally applied in the form of a mouth rinse. The aforesaid patent to Moss, U.S. Pat. No. 2,749,278, refers to a mouth rinse consisting of a dilute solution of sodium fluoride (5 parts per million F). Although the use of a mouth rinse composed of a solution of sodium fluoride in the stated concentration may have some effect in reducing prevalence of *Lactobacillus acidophilus* in saliva, and to that extent may reduce growth of cavities, it has not been shown sufficiently effective for preventing incipience of dental caries.

A mouth wash to prevent development of cavities in teeth has also been proposed in Patent to Sandberg, 2,527,686. According to that patent, the mouth wash consists of an aqueous composition of sodium fluoride, zinc chloride, formaldehyde, and certain ferments, the sodium fluoride being present in an amount not less that 15 grains per gallon nor more than 30 grains per gallon.

In my earlier patent, 2,913,373 mentioned above, we disclosed a fluoride mouth composition which was far more effective in preventing the incipience as well as the growth of dental caries than anything available prior to its invention and which at the same time was capable of retaining the gingiva or mucosa in healthy state. That composition consisted essentially of an aqueous solution of a water soluble fluoride as active agent and a surface active wetting agent of a character having no substantial effect in inactivating the fluoride, said wetting agent being present in a minor proportion relative to the fluoride present, the fluoride being present in a concentration of approximately one grain per ounce of solution. The mouth wash of my earlier patent has received wide acceptance and recognition in the dental profession (e.g. *Int. Dent. Journal*, Vol. 23, No. 4, pages 585–590, 1973).

Having in mind the general history of the inadequacies of prior art treatments I have continued to attempt to improve the mouth wash of my prior patent and have discovered that by slight modifications a new composition is produced which is remarkably more effective both in the prevention of dental caries as well as in retarding their growth and in the very desirable retention of the healthy state of the gingiva or mucosa and reduction of undesirable oral bacteria.

The modified composition of this invention, in addition to being more effective, provides an added element of safety for all ages by the additional ingredient which induces vomiting and the expellation of anything that might possibly be considered unsafe.

Accordingly it is a principal object of this invention to provide a mouth wash composition which will be highly efficacious in the prevention of dental decay and which may be safely used by persons of all ages.

Another object of the invention is to provide such a mouth wash composition which will be effective to prevent the incipience as well as the growth of dental caries in people of any age at which it can be effectively utilized, beginning at as young an age as two and half years.

Still another object of the invention is to provide a mouth wash composition which is capable, in use, not only of preventing the incipience as well as the growth of dental caries, but also capable of retaining the gingiva or mucosa in healthy state.

These and other objects and advantages of the invention will more readily appear from the detailed description of the invention given herebelow.

According to my invention, there is provided a mouth wash composition consisting essentially of a water-soluble fluoride, preferably sodium fluoride, as the active ingredient thereof, together with a minor amount of an anionic surface active wetting agent and a minor amount of sodium chloride. This composition is preferably in the form of a dry powder mix so that a stated quantity thereof dissolved in a stated amount of water will provide a solution in which the concentration of the sodium fluoride will be of the order of 1 grain per ounce of solution, or say, approximately 130 grains of the fluoride per gallon.

I have found, by actual clinical tests conducted over an extended period of time in actual practice, that a solution of this composition in the concentration above mentioned serves well to prevent the incipience and growth of cavities in teeth, when used in a quantity of three to four ounces, twice each day, preferably in the morning and before retiring. I have found that the composition is effective to secure that desirable result in persons of all ages, and may be used with complete safety when following simple instructions. Hence, the composition is not restricted, in its use, to particular age limits, but, rather, may be conveniently and effectively, used by young and old alike. These desirable results are, moreover, achieved without requiring the services of a dentist or supervised technician, such as is necessary in these instances where fluorides are topically applied in modes heretofore proposed.

I have found as a result of studies made in the course of my clinical tests, that the sodium fluoride in the concentration referred to herein, retards bacterial growth, exerts a bacteriostatic action and inhibits phosphatase. Thus, when used in a solution of the concentration contemplated herein, the prophylactic effect is not dependent alone upon a reduction in the prevalence of *Lactobacillus acidophilus* in saliva.

I have found that the use of an ionic surface active wetting agent and a small amount of sodium chloride provides a synergistic action with the fluoride in enhancing antibacterial potential of the fluoride and in inhibiting bacterial metabolism, as well as providing a built in safety factor.

Although I have referred specifically to the use of sodium fluoride, it should be evident that other soluble fluorides, such as stannous fluoride, potassium fluoride etc., may be employed, provided they are in equivalent or substantially equivalent concentration in water solution.

The wetting or surface active agent constitutes a minor proportion of the composition. As such, there may be employed any of the well-known wetting agents, provided the one selected is anionic and does not have any substantial effect in the direction of inactivation the fluoride. Preferably, there is employed a powdered form of wetting agent, such as one of the compounds produced and marketed by American Cyanamid and Chemical Corporation, under the trade names of Aerosol AY (diamyl sodium sulfosuccinate), Aerosol IB (dibuty sodium sulfosuccinate), and Aerosol OS (isopropylnaphthalene sodium sulfonate).

In any event, as above indicated, the surface active agent employed is one which will not react with or otherwise inactivate the soluble fluoride in the concentrations in which the surface active agent would be present when the mix is dissolved in the stated amount of water.

The sodium chloride also constitutes a minor proportion of the composition.

In my composition, a small amount of flavoring agent and/or sweeting agent may be added.

In general, a dry powder mix suitable for use in accordance with my invention, may be composed of the following ingredients in substantially the proportions indicated:

|  | Parts (by weight) |
|---|---|
| Sodium fluoride | 115 |
| Wetting agent | 0.1 |
| Saccharin | 1.2 |
| Sodium chloride | 12 |

A dry mix of the composition set forth above has been demonstrated to be effective when employed in aqueous solution in the concentration herein set forth, viz., such as will provide approximately one grain of the fluoride per ounce of solution. It will be understood, however, that various changes may be made in the composition without departing from the scope of the invention. Thus, as already indicated, other water soluble fluorides, such as stannous fluoride or potassium fluoride may be employed in lieu of the sodium fluoride; likewise other wetting agents, as well as other flavoring agents may be employed. The proportion of the wetting agent employed may vary, depending primarily upon its surface active properties and upon the particular fluoride employed and the nature of the tap water with which the dry powder mix is to be used for preparing the mouth wash solution.

In a preferred and specific embodiment of the invention, a dry powder mix in conformity with the above-stated general formula may be compounded and packaged in individual envelopes or other suitable containers, each containing the fluoride and other ingredients in amounts as follows:

| Sodium fluoride | grains | 288 |
|---|---|---|
| Aerosol AY (wetting agent) | " | ¼ |
| Salt (NaCl) | " | 30 |
| Saccharin | " | 3 |
| Flavoring agent | minims | 15 |

If desired, appropriate amounts of a suitable dye may also be added as coloring.

With envelopes containing the fluoride and other ingredients in amounts above stated, the user would be instructed, preferably by imprinting suitable directions on each envelope, to dissolve the contents thereof in one quart of distilled or pre-boiled water, and to use one tablespoonful of this solution in one-half glass of water as a mouth wash solution, after first cleansing the teeth and rinsing all tooth cleansing material from the teeth and mouth. The patient is also instructed to use the mouth wash both in the morning and before retiring, by vigorously and thoroughly rinsing the mouth and teeth, but with care not to swallow any portion of the mouth wash.

It will be seen that when the above-stated contents of an envelope of the dry mix are dissolved and diluted as indicated, the concentration of sodium fluoride in the final solution employed as the mouth wash will represent about 135 grains of sodium fluoride per gallon of water, or fractionally more than one grain per ounce, and hence about 3 to 4 grains per use.

Data accumulated over an extended period of time by recognized bio-statisticians reveal that by the use of my mouth wash there was an observed reduction of dental decay amounting, after two years, to 88.4%; after four years, the reduction amounted to 87.1%; after six years, the reduction amounted to 86%; after 8 years, 89.6% and after ten years, it amounted to 87.7%. These observations further show that when the composition of my invention is prepared and utilized as herein set forth, and with substantial regularity, the progress of incipient caries appears to be arrested; white decalcified lesions which previously were not penetrable with a sharp explorer remain intact, no further decalcification being noted after long periods of observation, the mouth remains cleaner, fewer stains appear on the teeth, the mucosa appears healthier, pits and fissures are less penetrable, and the enamel appears more highly glazed. On the other hand, when use of the mouth wash is discontinued, the mouth reverts to its original state and decay frequently is again initiated.

If desired, the composition of my invention may be furnished for use in the form of compressed but readily disintegratable type of tablets, each containing three grains of the fluoride and proportional amounts of wetting agent, sodium chloride and other ingredients, so that when dissolved in three to four ounces of water, it will provide a solution of the desired concentration of flurodie for use in accordance herewith.

Also, if desired, the composition may be furnished as a pre-formed solution in water, wherein the concentration of the fluoride is of the order of 135 grains per gallon and hence useable as such in a quantity of one-half glass thereof per use; or wherein the concentration of the fluoride is of the order of 288 grains per quart, requiring the user only to mix one tablespoonful thereof with one-half glass of water for each use.

Due to the toxicity of sodium fluoride, and having in mind that the composition of my invention is designed and intended for individualistic application by lay people, it is recommended that the composition, in the several forms mentioned, be dispensed on prescription and by responsible parties.

The foregoing detailed description has been given for purposes of explaining and illustrating the invention. It is accordingly to be understood that the invention is not limited to the detailed information set forth, and that various modifications may be made therein without departing from the scope of the invention as defined by the appended claims.

I claim:

1. A mouth wash adapted to prevent dental caries of the teeth, consisting essentially of an aqueous solution of a water-soluble fluoride as active agent, sodium chloride and an anionic surface active wetting agent of a character having no substantial effect in inactivating the fluoride, said sodium chloride being present in a small but effect amount to increase the effectiveness of the fluoride to prevent incipience of dental caries and said wetting agent being present in minor proportion relative to the amount of said fluoride present, said fluoride being present in a concentration of approximately one grain per ounce of the solution.

2. A mouth wash as defined in claim 1, wherein said active agent is sodium fluoride.

3. A dry powder mix consisting essentially of a water-soluble fluoride, sodium chloride and an anionic surface active wetting agent having no substantial effect in inactivating said fluoride, in proportions of approximately 115 parts of the fluoride to 12 parts of sodium chloride and one part of the wetting agent, by weight, said mix being adapted to prevent dental caries when used as a mouth wash in an aqueous solution in which the concentration of said fluoride is approximately one grain per ounce.

4. A dry powder mix as defined in claim 3, wherein said soluble fluoride is sodium fluoride.

5. As an article of manufacture, a single dosage unit packaged dry powder mix, consisting essentially of the following ingredients in the amounts set forth, namely:

| Sodium fluoride | grains | 288 |
|---|---|---|
| Aerosol Ay (diamyl sodium sulfosuccinate) | '' | ¼ |
| Salt (NaCl) | '' | 30 |
| Saccharin | '' | 3 |
| Flavoring agent | minims | 15 | and adapted to prevent dental caries when employed as a mouth wash in an aqueous solution in which the concentration of sodium fluoride is approximately one grain per ounce.

6. As an article of manufacture, a compressed disintegratable table consisting essentially of approximately three grains of a water-soluble fluoride, .3125 grains of salt and 0.0025 grain of a surface active wetting agent of a character having no substantial effect in inactivating the fluoride, said tablet being adapted to prevent dental caries when used as a mouth wash in a solution of approximately three ounces of water.

7. The article defined in claim 6, wherein said fluoride is sodium fluoride.

8. A composition consisting essentially of a water-soluble fluoride, sodium chloride and a surface active wetting agent in a solution of water, said wetting agent being of a character having no substantial effect in inactivting the fluoride, said sodium chloride being present in a small but effective amount to increase the effectiveness of the fluoride in preventing incipience and growth of dental caries, and wetting agent being present in minor proportion relative to the amount of said fluoride present, said fluoride being present in said solution in a concentration corresonding approximately to 288 grains per quart of solution, said solution being adapted to prevent dental caries when used as a mouth wash in a dilution in the range of 6 to 8 parts of water per part of said solution.

9. A composition as defined in claim 8, wherein said fluoride is sodium fluoride.

* * * * *